US00PP12411P2

(12) United States Plant Patent
Hanes

(10) Patent No.: US PP12,411 P2
(45) Date of Patent: Feb. 19, 2002

(54) GERANIUM PLANT NAMED 'CLIPS ROSE'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/542,050

(22) Filed: Mar. 31, 2000

(51) Int. Cl.[7] ..... A01H 5/00
(52) U.S. Cl. ..... Plt./329
(58) Field of Search ..... Plt./324, 325, 327, Plt./328, 329

(56) References Cited

PUBLICATIONS

GTITM UPOVROM Citation for 'Clips Rose' as per QZ PBR 980871; Jun. 26, 1998.*
GTITM UPOVROM Citation for 'Clips Rose' as per CA PBR 98–1460; Aug. 21, 1998.*

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new geranium cultivar particularly distinguished by dark green foliage with light zonation, rose flower color, and semi-double flowers on large umbels, fast rooting and exhibits vigorous growth.

1 Drawing Sheet

BACKGROUND OF THE NEW PLANT

Figure 1:
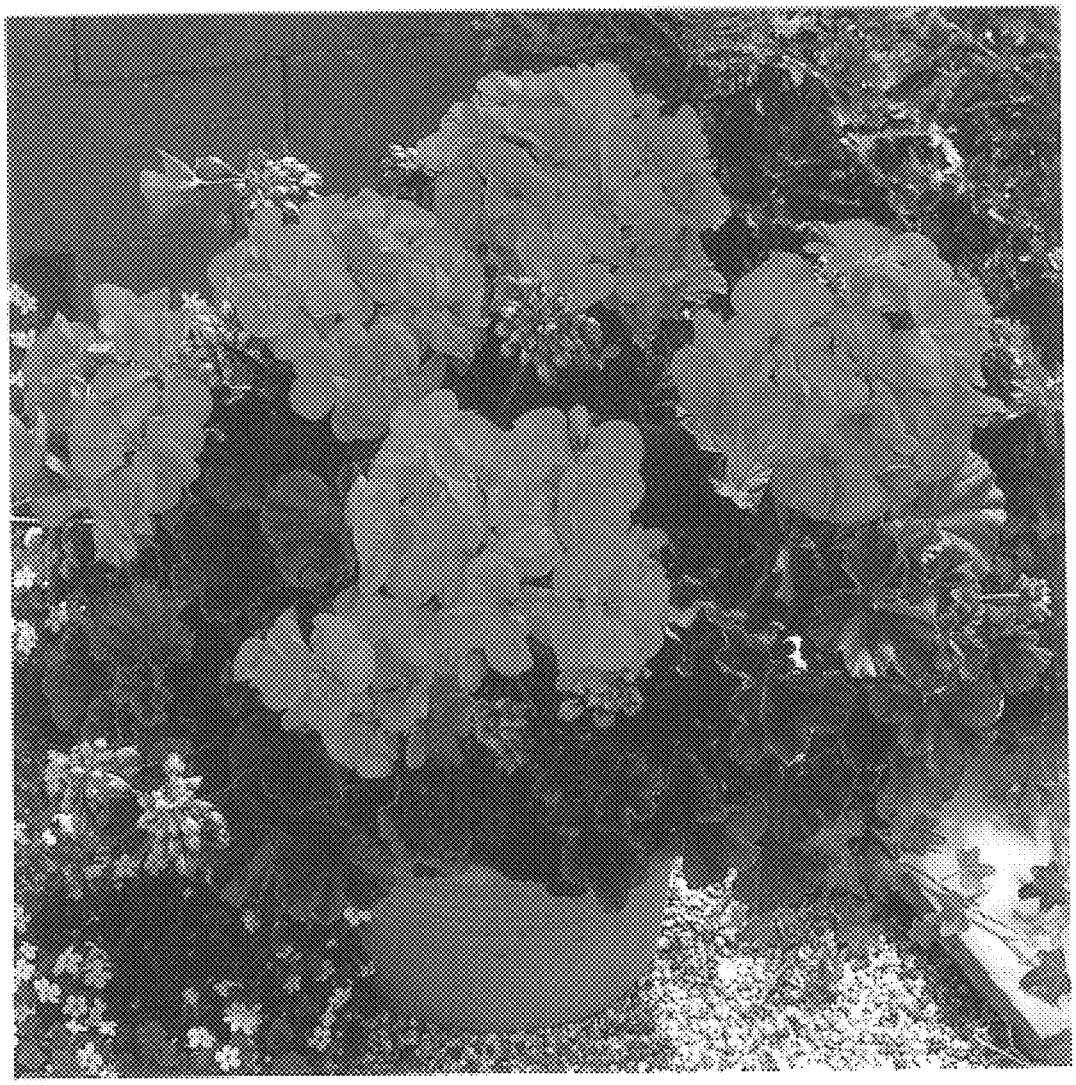

The present invention comprises a new and distinct cultivar of geranium, botanically known as *Pelargonium hortorum* Bailey, and herinafter referred to by the cultivar name 'Clips Rose'. The new cultivar originated from a cross of the seed parent 5034-1 (unpatented) and the pollen parent 4911-1 (unpatented).

'Clips Rose' is a product of a planned breeding program intended to create new geranium cultivars with rose colored flowers, semi-double flower form, dark green foliage, vigorous growth and superior cutting productivity.

The new cultivar was created in 1995 in Gilroy, Calif. and has been repeatedly asexually reproduced by cuttings in Gilroy, Calif. and Guatemala over a four year period. The new cultivar has also been trialed at Okemos, Mich.; Andijk, The Netherlands and St. Albert, Alberta, Canada. The new cultivar has been found to retain its distinctive characteristics through successive propagations; and are firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Clips Rose'. The data which defines these characteristics were collected from asexual reproductions carried out in Gilroy, Calif. The plant history was taken on 12 week old plants, blossomed under natural light in a greenhouse and color readings were taken in the greenhouse in Gilroy, Calif. on Feb. 15, 2000 at 2:00 p.m. under ambient light. Color references are primarily to the R.H.S. Colour Chart of The Royal Horticultural Society of London (R.H.S.).

The Plant

Classification:
- *Botanical.*—*Pelargonium hortorum* Bailey.
- *Commercial.*—Zonal geranium.

Form: Upright intermediate plant.

Size: 12 cm, as a 10 cm pot plant, excluding blooms; plant height from soil level to top of umbels is 25 cm; 45 cm wide.

Strength: Good shipping ability as rooted or unrooted cuttings.

Time to produce a finished flowering plant: 12 weeks.

Foliage: Abundant quantity; lateral branch length is 5–18 cm (depending on age of the branch); internode length is 2–3 cm; internode color is geen (RHS 146D).

Roots: Time to initiate roots is 9–10 days and time to develop roots is 27 days; description of roots is fibrous yet coarse.

Leaves:
- *Size.*—Diameter about 7–8.5 cm; length of younger smaller leaves are 3–3.5 cm; older larger leaves are 4–6 cm; apex is obtuse; base is cordate.
- *Shape.*—Rounded cordate with occasional upfolding between veins.
- *Margin.*—Irregularly crenate.
- *Texture.*—Leathery and pubescent on both surfaces, especially along veins.
- *Ribs and veins.*—Distinctly palmate, 1.9 to 4.0 cm long.
- *Color.*—Upper side: Dark Green — a color between RHS 147A and 147-B with slightly darker green zonation of RHS 147A. Under side: Dark Green — RHS 147B. Ribs and veins not prominently different from upper surface.
- *Petioles.*—About 4.5 to 6.4 cm in length; 2–3 mm in diameter; green RHS 146B.

The Bud

Size:
- *Diameter.*—About 8 mm
- *Length.*—About 1.0 cm to 1.4 cm at time of bud opening. .

Shape: Pointed ovoid.

Color: Petals when sepals first divide is RHS 66B.

Sepals: 5 in number, flat behind petals. Pointed linear lanceolate; length is 1 cm; width 4 mm; base is truncate; upper and lower color is green RHS 146B with the bottom 0.5 mm being red RHS 59A.

The Flower

Flowering season: Continuous throughout the year.

Size: Approximately 4.5 cm diameter, 1.5 cm deep, irregularly radially symmetrical.

Form: Cup-shaped when bloom first opens, later flattening to shallow cup shape with maturity.

Petals/petaloids: Shape is obovate; apex is obtuse; base is attenuate; margin is entire; 5–6 imbricate petals, 1.8–2.0 cm wide and approximately 2.3 cm long. 3–5 smaller petaloids of varying shape; 1.5 cm in length and 1 cm width; top two petals upper color is red-purple RHS 61C with a lighter flare of RHS 61D near the petal base and on top of the lighter flare are stripes (veins) of RHS 61C; lower surface of upper two petals is a red-purple color between RHS 61C and 61D; bottom petals and all petaloids are red-purple RHS 67B on the upper surface and RHS 67C on the lower surface. Petals and petaloids soft and satiny.

Pedicel: Approximately 2.4 cm in length; grey-purple RHS 183D.

Persistence: Non-shattering flower.

Inflorescence

Type: An umbel with a depth of 5–5.5 cm composed of approximately 24 flowers, erect or laterally ascending that has a diameter of approximately 9 cm and is held about 6 cm above the foliage.

Peduncle: Approximately 5–10 cm in length, mostly 10 cm. Green RHS 146C with portions of a reddish tint RHS 183D where it has been exposed to more sunlight.

Reproductive Organs

Stamens:

*Anthers.*—6–8 positioned below the mature stigma, orange-red prior to anthesis.

*Filaments.*—White near base and mid length, graduating to rose red RHS 57C near anther.

*Pollen.*—Moderate amount; Orange RHS 28B.

Pistil:

*Number.*—1.

*Length.*—Approximately 8 mm.

*Stigma.*—5 linear lobes of near equal length, curling back toward ovary, rose red in color.

*Style.*—Length: About 3 mm. Color: Rose red.

*Ovaries.*—At anthesis, densely pubescent with white hairs, oblong. Green at base, purplish-brown upper two thirds, drying to a light brown at maturity.

Fruit/seeds: Partially fertile; maximum of 5 seeds per spike; seed length is approximately 4–4.5 mm; width is 1.7–2.0 mm; color is brown RHS 165A.

Disease/Insect Resistance

No observed disease or pest susceptibility or resistance.

Comparison with Parental Cultivars

When compared to the parental cultivars 5034-1 and 4911-1, 'Clips Rose' has a bright rose flower color while 5034-1 has a red flower. Compared to 4911-1, 'Clips Rose' is a larger, more basal branched plant.

I claim:

1. A new and distinct cultivar of geranium plant substantially as herein shown and described, named 'Clips Rose', that is characterized by: dark green foliage with light zonation, rose flower color, and semi-double flowers on large umbels, fast rooting and exhibits vigorous growth habit.

* * * * *